United States Patent
Glukhovsky et al.

(10) Patent No.: US 7,347,817 B2
(45) Date of Patent: Mar. 25, 2008

(54) POLARIZED IN VIVO IMAGING DEVICE, SYSTEM AND METHOD

(75) Inventors: Arkady Glukhovsky, Santa Clarita, CA (US); Amit Pascal, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 200 days.

(21) Appl. No.: 11/173,153

(22) Filed: Jul. 5, 2005

(65) Prior Publication Data

US 2006/0036131 A1    Feb. 16, 2006

Related U.S. Application Data

(63) Continuation-in-part of application No. 10/208,832, filed on Aug. 1, 2002, now abandoned.

(60) Provisional application No. 60/309,181, filed on Aug. 2, 2001.

(51) Int. Cl.
*A61B 1/04* (2006.01)
*A61B 1/06* (2006.01)

(52) U.S. Cl. ............... 600/181; 600/160; 600/179; 600/473; 600/476

(58) Field of Classification Search ........... 600/181, 600/160, 179, 473, 476
See application file for complete search history.

(56) References Cited

U.S. PATENT DOCUMENTS

| | | | |
|---|---|---|---|
| 3,971,362 A | 7/1976 | Pope et al. | |
| 4,278,077 A | 7/1981 | Mizumoto | |
| 4,631,582 A * | 12/1986 | Nagasaki et al. | 348/69 |
| 4,668,860 A * | 5/1987 | Anthon | 250/225 |
| 4,689,621 A | 8/1987 | Kleinberg | |
| 4,844,076 A | 7/1989 | Lesho et al. | |
| 4,936,823 A | 6/1990 | Colvin et al. | |
| 5,241,170 A | 8/1993 | Field et al. | |
| 5,279,607 A | 1/1994 | Schentag et al. | |
| 5,406,938 A * | 4/1995 | Mersch et al. | 600/138 |
| 5,604,531 A | 2/1997 | Iddan et al. | |
| 5,697,384 A | 12/1997 | Miyawaki et al. | |
| 5,812,187 A | 9/1998 | Watanabe | |

(Continued)

FOREIGN PATENT DOCUMENTS

DE    34 40 177    5/1986

(Continued)

OTHER PUBLICATIONS

"Robots for the future"—Shin-ichi, et al , printed Nov. 29, 2001.

(Continued)

*Primary Examiner*—John P. Leubecker
(74) *Attorney, Agent, or Firm*—Pearl Cohen Zedek Latzer, LLP

(57) ABSTRACT

An autonomous in vivo sensing device may include a polarizing filter to polarize light emitted by an illumination unit, and to block light specularly reflected from a turbid media from reaching an imager of such device. An autonomous in vivo sensing device with monochromatic illumination units to alternatingly illuminate a target area with light of different wavelengths, and to subtract an image illuminated by light in a first wavelength from an image illuminated by light in a second wavelength, to produce an image of a sub-surface layer of such target area.

28 Claims, 10 Drawing Sheets

U.S. PATENT DOCUMENTS

| | | |
|---|---|---|
| 5,819,736 A | 10/1998 | Avny et al. |
| 5,908,294 A | 6/1999 | Schick et al. |
| 5,929,901 A | 7/1999 | Adair et al. |
| 5,993,378 A | 11/1999 | Lemelson |
| 6,088,606 A | 7/2000 | Ignotz et al. |
| 6,177,984 B1 * | 1/2001 | Jacques ............. 356/39 |
| 6,240,312 B1 | 5/2001 | Alfano et al. |
| 6,449,006 B1 | 9/2002 | Shipp |
| 6,772,003 B2 * | 8/2004 | Kaneko et al. ............. 600/476 |
| 2001/0051766 A1 | 12/2001 | Gazdzinski et al. |
| 2002/0054290 A1 * | 5/2002 | Vurens et al. ............. 356/369 |
| 2002/0068853 A1 * | 6/2002 | Adler .................. 600/160 |
| 2002/0087047 A1 * | 7/2002 | Remijan et al. ............. 600/109 |
| 2002/0103417 A1 | 8/2002 | Gazdzinski |
| 2002/0171669 A1 | 11/2002 | Meron et al. |
| 2002/0193664 A1 | 12/2002 | Ross et al. |
| 2002/0198439 A1 | 12/2002 | Mizuno |
| 2003/0167000 A1 | 9/2003 | Mullick et al. |
| 2003/0174208 A1 | 9/2003 | Glukhovsky et al. |
| 2003/0208107 A1 | 11/2003 | Refael |
| 2004/0111031 A1 * | 6/2004 | Alfano et al. ............. 600/476 |
| 2004/0249274 A1 * | 12/2004 | Yaroslavsky et al. ....... 600/431 |
| 2005/0165279 A1 * | 7/2005 | Adler et al. ............. 600/181 |
| 2005/0182295 A1 * | 8/2005 | Soper et al. ............. 600/117 |
| 2005/0283065 A1 * | 12/2005 | Babayoff ............. 600/407 |
| 2006/0195014 A1 * | 8/2006 | Seibel et al. ............. 600/102 |

FOREIGN PATENT DOCUMENTS

| | | |
|---|---|---|
| JP | 57-45833 | 3/1982 |
| JP | 4109927 | 4/1992 |
| JP | 1992-144533 | 5/1992 |
| JP | 5015515 | 1/1993 |
| JP | 2001224553 | 8/2001 |
| WO | WO 01/08548 | 2/2001 |
| WO | WO 01/50941 | 7/2001 |
| WO | WO 01/65995 | 9/2001 |

OTHER PUBLICATIONS

"The Radio Pill, Rowlands". et al ., British Communications and Electronics. Aug. 1960, pp. 598-601.

"Video Camera to "TAKE""—RF System lab Dec. 25, 2001.

"Wellesley company sends body montiors into space"—Crum. Apr. 1998.

www rfnorkia com—NORIKA3, Jan. 1, 2002.

'Wireless transmission of a color television moving image from the stomach using a miniature CCD camera, light source and microwave transmitter', Swain CP, Gong F. Mills TN Gastrointest Endosc 1997;45:AB40.

BBC News Online—Pill camera to 'broadcast from the gut'. Feb. 21, 2000 www news bbc co uk.

Deep subsurface imaging in tissues using spectral and polarization filtering S G Demos Jul. 3, 2000/vol. 7, No. 1 Optics Express.

International Search Report for Application No. PCT/IL06/00780. Dated: Jun. 13, 2007.

* cited by examiner

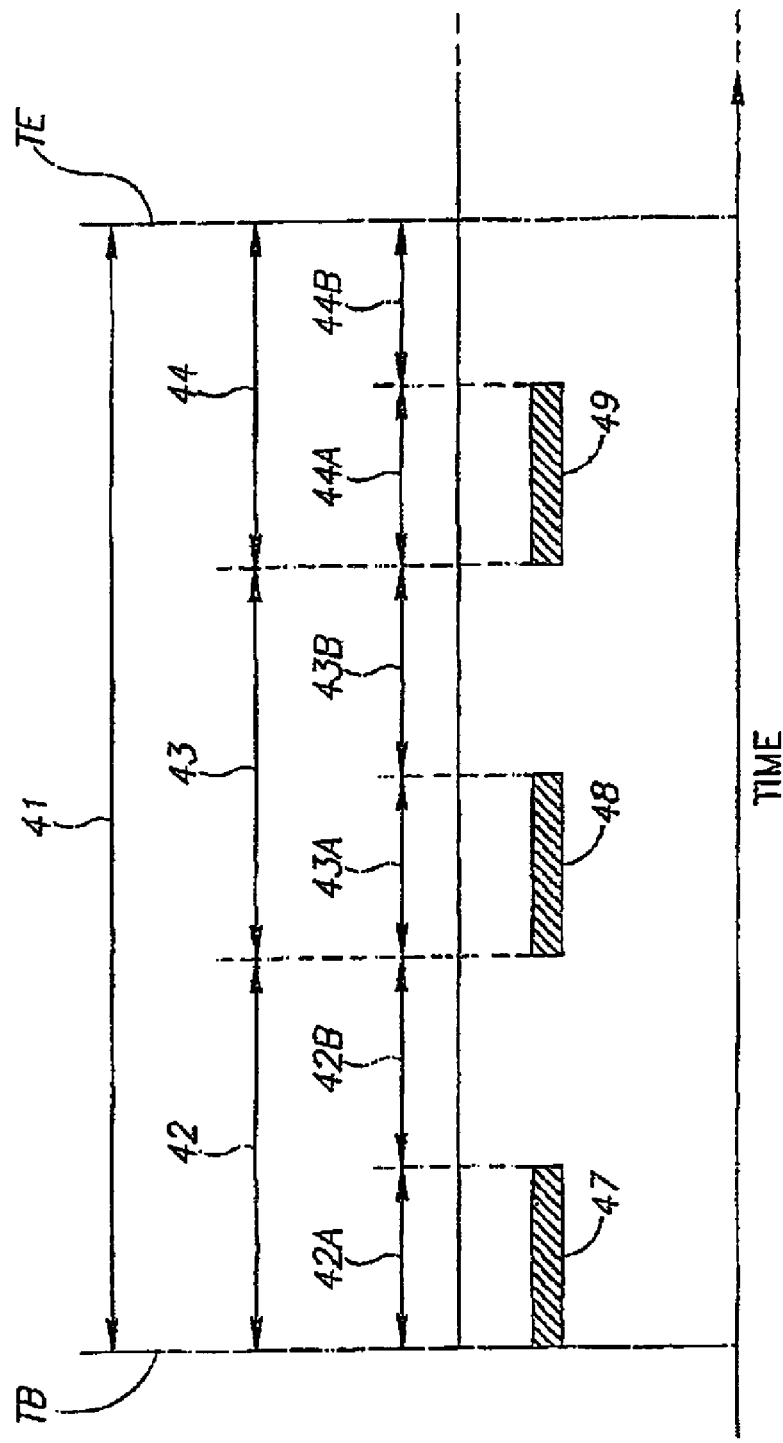

POLARIZED IN VIVO IMAGING DEVICE, SYSTEM AND METHOD

CROSS REFERENCE TO RELATED APPLICATIONS

The present application is a continuation-in-part of U.S. patent application Ser. No. 10/208,832 filed on Aug. 1, 2002 now abandoned and entitled In Vivo System Device and Method, which claimed benefit from prior provisional application No. 60/309,181 entitled "IN VIVO IMAGING METHODS AND DEVICES" and was filed on Aug. 2, 2001. All of such applications are incorporated by reference herein in their entirety.

FIELD OF THE INVENTION

The present invention relates to the field of in-vivo imaging.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities Reference is now made to FIG. 1 which is a schematic diagram illustrating an example of a prior art autonomous in-vivo imaging device. The device 10A typically includes a capsule-like housing 18 having a wall 18A. The device 10A has an optical window 21 and an imaging system for obtaining images from inside a body cavity or lumen, such as the GI tract. The imaging system may include an illumination unit 23. The illumination unit 23 may include one or more light sources 23A. The one or more light sources 23A may be a white light emitting diode (LED), or any other suitable light source, known in the art. The imaging system of the device 10A includes an imager 24, which acquires the images and an optical system 22 which focuses the images onto the imager 24.

In some configurations when a capsule or tube shaped device is used, the imager 24 may be arranged so that its light sensing surface 28 is perpendicular to the longitudinal axis of the device 40. Other arrangements may be used.

The illumination unit 23 illuminates the inner portions of the body lumen through an optical window 21. Device 10A further includes a transmitter 26 and an antenna 27 for transmitting the video signal of the imager 24, and one or more power sources 25. The power source(s) 25 may be any suitable power sources such as but not limited to silver oxide batteries, lithium batteries, or other electrochemical cells having a high energy density, or the like The power source(s) 25 may provide power to the electrical elements of the device 10A.

Typically, in the gastrointestinal application, as the device 10A is transported through the gastrointestinal (GI) tract, the imager, such as but not limited to the multi-pixel imager 24 of the device 10A, acquires images (frames) which are processed and transmitted to an external receiver/recorder (not shown) worn by the patient for recording and storage. The recorded data may then be downloaded from the receiver/recorder to a computer or workstation (not shown) for display and analysis.

During the movement of the device 10A through the GI tract, the imager may acquire frames at a fixed or at a variable frame acquisition rate. For example, in one example the imager (such as, but not limited to the imager 24 of FIG. 1) may acquire images at, for example, a fixed rate of two frames per second (2 Hz) However, other different frame rates may also be used, depending, inter alia, on the type and characteristics of the specific imager or camera or sensor array implementation that is used, and on the available transmission bandwidth of the transmitter 26. The downloaded images may be displayed by the workstation by replaying them at a desired frame rate. In this way, the expert or physician examining the data is provided with a movie-like video playback, which may enable the physician to review the passage of the device through the GI tract.

Decreasing the cross-sectional area of such devices may be limited by the cross-sectional area of the imaging sensor, such as for example the imager 24 of FIG. 1. In order to decrease the size and the cross sectional area of the imaging sensor one may need to reduce the pixel size.

In certain imaging sensors, the area of a single pixel cannot be indefinitely reduced in size because the sensitivity of the pixel depends on the amount of light impinging on the pixel which in turn may depend on the pixel area.

Typically, color imaging in imaging sensors may be achieved by using an array of color pixels. For example, in a color image sensor such as the imaging sensor 24 of the device 10A of FIG. 1, there may be three types of pixels in the imager. Each type of pixel may have a special filter layer deposited thereon. Generally, but not necessarily, the filters may be red filters, green filters and blue filters (also known as RGB filters). The use of a combination of pixels having red, green and blue filters is also known in the art as the RGB color imaging method. Other color imaging methods may utilize different color pixel combinations, such as the cyan-yellow-magenta color pixels (CYMK) method.

The pixels with the color filters may be arranged on the surface of the imager in different patterns. For example, one type of color pixel arrangement pattern is known in the art as the Bayer CFA pattern (originally developed by Kodak™). Other color pixel patterns may also be used.

A problem encountered in the use of RGB color pixel arrays within in-vivo imaging device such as swallowable capsules, or catheter-like devices, or endoscopes, or endoscope like devices, is that for color imaging, one typically needs to use imagers having multiplets of color pixels. Thus, for example in an imager using RGB pixel triplets, each triplet of pixels roughly equals one image pixel because a reading of the intensities of light recorded by the red pixel, the green pixel and the blue pixel are required to generate a single color image pixel. Thus, the image resolution of such a color image may be lower than the image resolution obtainable by a black and white imaging sensor having the same number of pixels. The converse of this is that for a given number of pixels a greater area may be needed for the imager.

A further problem encountered in in-vivo imaging with an autonomous device is the reflection by a turbid media such as liquids or particles floating in a body lumen of light emitted by an illumination unit 23 Such reflected light may cloud or impair an image of a target tissue or wall of a body lumen.

A further problem encountered in in-vivo imaging with an autonomous device is the limitation of images that can be captured to images of the upper surface of a wall of a body lumen. Characteristics such as pathologies of lower layers of tissues may not be clearly visible in in-vivo images captured by prior art autonomous in vivo devices.

BRIEF DESCRIPTION OF THE DRAWINGS

The invention is herein described, by way of example only, with reference to the accompanying drawings, in which like components are designated by like reference numerals, wherein:

FIG. 3 is a schematic timing diagram illustrating an exemplary timing schedule which may be usable for performing color imaging in the imaging device illustrated in FIG. 2A;

SUMMARY OF THE INVENTION

Figure 1:
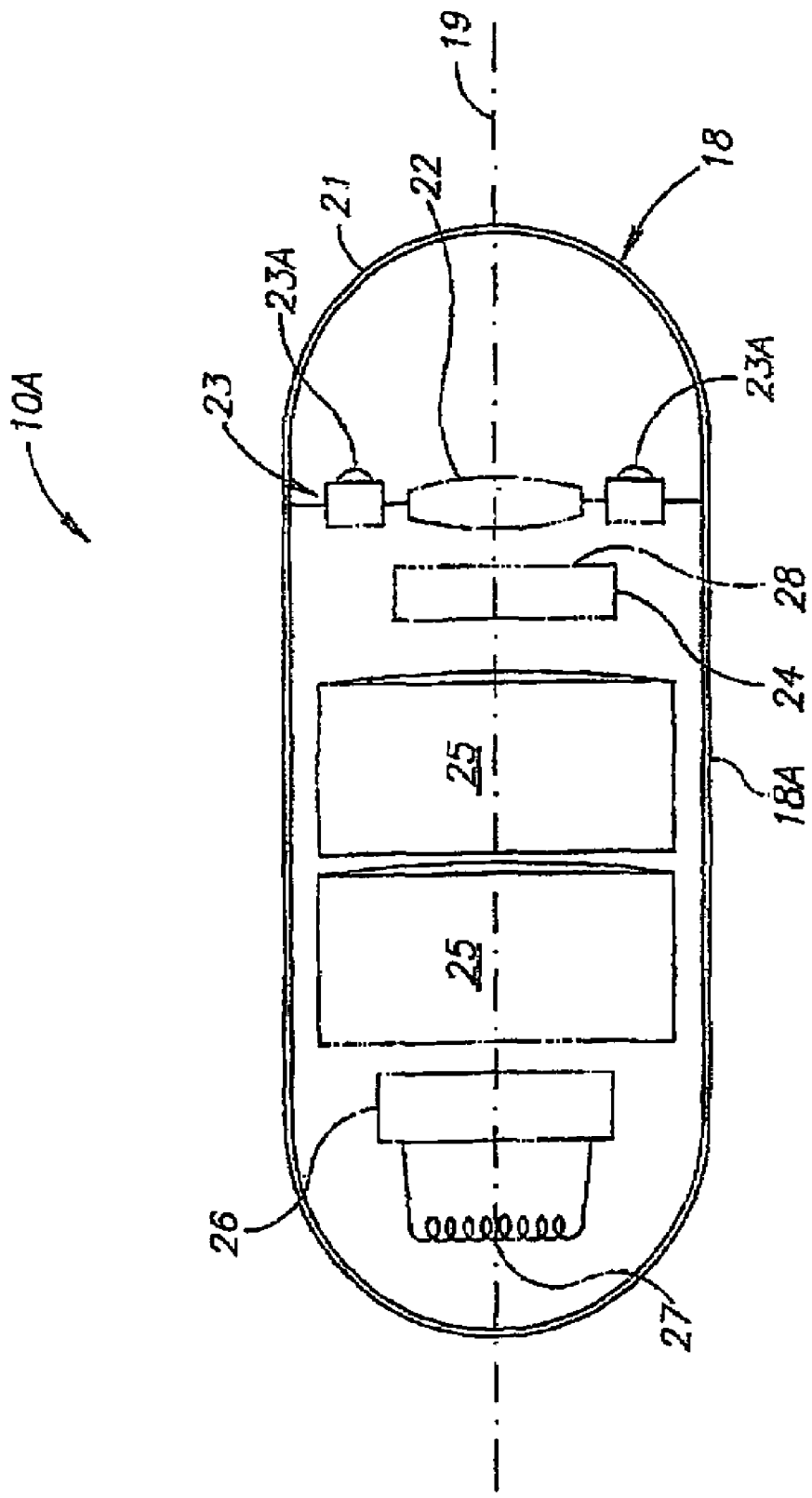
FIG. 1 is a schematic diagram illustrating an example of a prior art autonomous in-vivo imaging device.

Embodiments of the invention may include an autonomous in vivo device that may have an illumination unit, a polarizer to polarize light from the illumination unit, an imager and a filter to block polarized light from reaching the imager. In some embodiments, the invention may include an optical dome over the illumination unit, and the optical dome may include the polarizer or polarizing filter. In some embodiments the polarizer may be configured orthogonally to light beams emitted by an illumination unit. In some embodiments, the polarizer may be curved or shaped as a hemisphere and may block polarized light specularly reflected from a turbid media, while allowing light in a polarization opposite to the polarized light to reach the imager. In some embodiments such opposite polarized light may have been diffused in an endo-luminal tissue. In some embodiments, the polarizer may include a liquid crystal.

In some embodiments, the invention may include one or more illumination units that may surround the imager. For example a first monochromatic illumination unit may emit light at from 300 nm to 450 nm, a second monochromatic illumination unit may emit light at from 450 nm to 700 nm, and a third monochromatic light unit may emit light at from 700 nm to 1100 nm In some embodiments, the invention may include a switch to coordinate an illumination by an illumination unit with an activation of the polarizer or polarizing filter.

In some embodiments, the invention may include a switch to activate a first monochromatic illumination unit independently of a second monochromatic illumination unit.

In some embodiments, a switch may activate a monochromatic illumination unit to emit a monochromatic light beam, and may activate the polarizer to polarize the light beam in a first polarization state, and to then polarize the light beam in a second polarization state. In some embodiments the invention may include a memory to store image data collected by the imager and such image data may include image data of a target area illuminated by a light beam polarized in a first polarization state, and image data of the target area illuminated by a light beam polarized in a second polarization state.

The invention may include an immobilizer to immobilize the device adjacent to an endo-luminal target area.

In some embodiments the invention may include a system that may include an autonomous in vivo sensing device having one or more monochromatic illumination units, an imager and a switch to activate a monochromatic illumination unit independently of another monochromatic illumination unit. In some embodiments the system may include a processor to subtract image data of a target area that may be illuminated by a first monochromatic illumination unit, from image data of a target area, that may be illuminated by a second monochromatic illumination unit. In some embodiments, the system may include a first monochromatic illumination unit to emit a light beam having a wavelength of between 300 nm and 450 nm, a second monochromatic illumination unit to emit a light beam having a wavelength of between 450 nm and 700 nm, and a third monochromatic illumination unit to emit a light beam having a wavelength of between 700 nm and 1100. In some embodiments, the system may include a polarizer to polarize light emitted by the illumination units and a filter to block polarized light from reaching an imager.

In some embodiments, a method of the invention may include illuminating a target area with light, polarizing the light and blocking with a filter such polarized light from reaching an imager.

In some embodiments, a method may include blocking the polarized light from reaching the imager of the device, where such blocked light was specularly reflected from a turbid media.

In some embodiments, a method may include illuminating a target area with light from one or more monochromatic illumination units.

In some embodiments, a method may include polarizing to a first polarization state a first light beam and polarizing to a second polarization state a second light beam.

In some embodiments, the method may include activating two monochromatic illumination units and subtracting image data of the target area illuminated by a first monochromatic illumination unit from image data of the target area illuminated by a second monochromatic illumination unit.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Some embodiments of the present invention are based on providing within an in vivo imaging device an imaging pixel array sensor having, typically, a small cross-sectional area using, for example, gray scale imaging pixels without color filters. Such an imaging sensor may be used in conjunction with a plurality of light sources having different spectral characteristics which provide successive or sequential illumination of a site imaged by the image sensor with, for example, light having specific spectral characteristics and bandwidth as disclosed in detail hereinafter. Such a system may allow the same pixel to be used to image more than one color or spectrum, increasing the spatial or other efficiency of the imager. Typically, the illumination provide includes visible light, but other spectra may be used.

Embodiments of such an imaging method may be used for implementing in vivo imaging systems and devices such as, but not limited to, swallowable autonomous in-vivo imaging devices (capsule-like or shaped otherwise), and wired or wireless imaging units which are integrated into endoscope-like devices, catheter-like devices, or any other type of in-vivo imaging device that can be introduced into a body cavity or a lumen contained within a body.

It is noted that while the embodiments of the invention shown hereinbelow are adapted for imaging of the gastrointestinal (GI) tract, the devices, systems and methods disclosed may be adapted for imaging other body cavities or spaces.

Figure 2A:
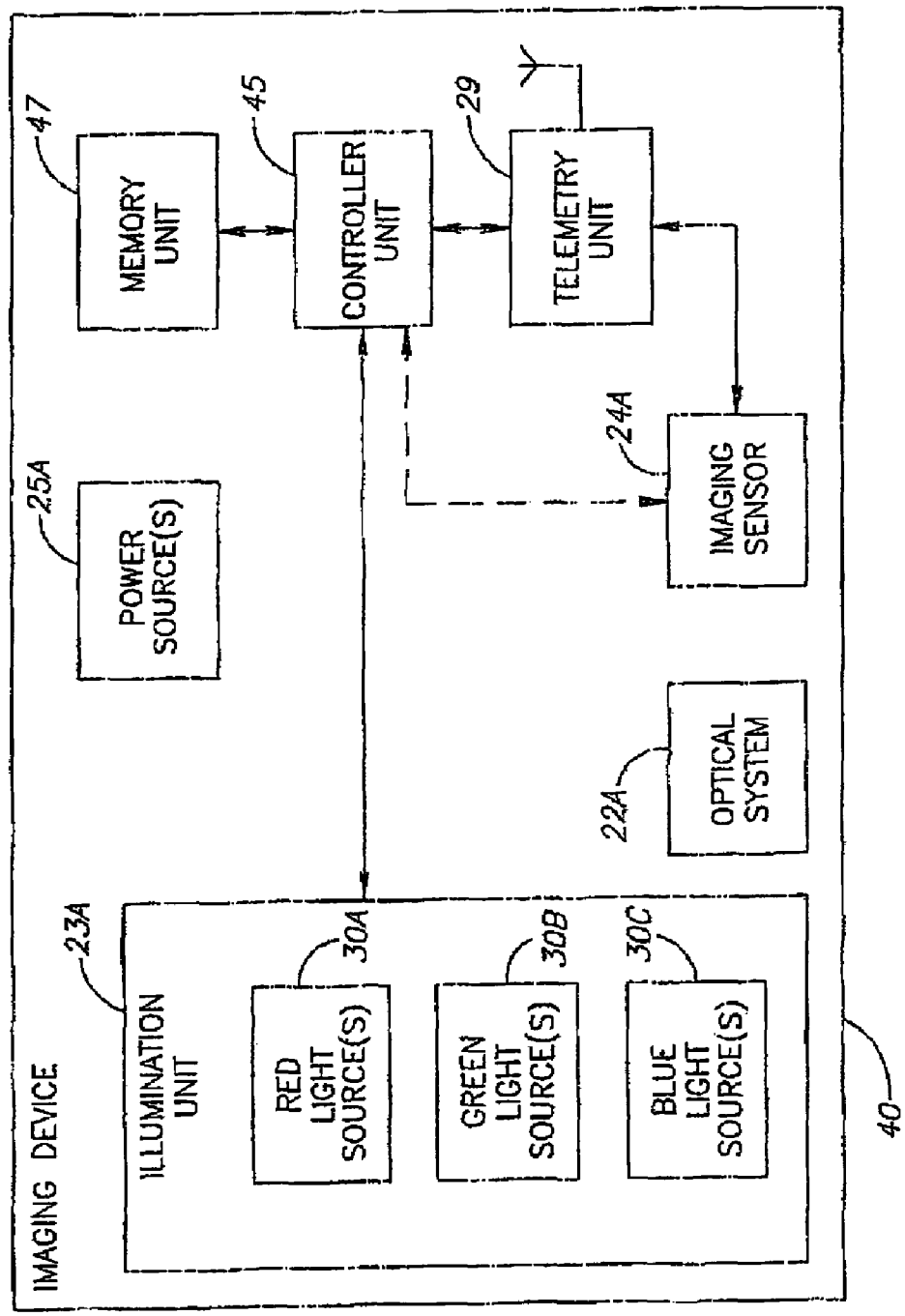
FIG. 2A is a schematic functional block diagram illustrating an in vivo imaging device, in accordance with an embodiment of the present invention.

Reference is now made to FIG. 2A which is a schematic functional block diagram illustrating an in vivo imaging device, in accordance with an embodiment of the present invention. In some embodiments, the device and its use are similar to embodiments disclosed in U.S. Pat. No. 5,604,531 to Iddan et al. and/or WO 01/65995 entitled "A Device And System For In Vivo Imaging", published on 13 Sep. 2001, both of which are hereby incorporated by reference. In other embodiments, other in-vivo imaging devices, receivers and processing units may be used.

The device 40 may include, for example, an optical system 22A and an imaging sensor 24A. The optical system 22A may be similar to the optical system 22 of FIG. 1 as disclosed hereinabove. The optical system 22A may include one or more optical elements (not shown) which are integrated with the optical system 22A or with another part of device 40, such as for example, a single lens (not shown in FIG. 2) or a compound lens, or any other combination of optical elements, including but not limited to lenses, mirrors, optical filters, prisms or the like, which may be attached to, or mounted on, or fabricated on or adjacent to the light sensitive pixels (not shown) of the imaging sensor 24A.

The imaging sensor 24A may be, for example, a CMOS imaging sensor suitable for gray scale imaging as is known in the art for CMOS sensors having no color filters deposited thereon (except for optional optical filters, such as infrared filters, which may be deposited on the pixels or which may be included in the optical system 22A). Typically the imaging sensor 24A is a monochrome sensor. For example, the CMOS sensor may be capable for producing, in response to being illuminated by light, an output representative of 256 gray levels sensed by each of the pixels (not shown) The number of the pixels in the imaging sensor may vary depending on the specific device or application. For example, the imaging sensor may comprise a 256×256 CMOS pixel array. Other types of sensors which may have different pixel numbers, may however also be used. For example, a CCD may be used.

The device 40 may also include a transmitter or telemetry unit 29 which may be (optionally) suitably connected to the imaging sensor 24A for telemetrically transmitting the images acquired by the imaging sensor 24A to an external receiving device (not shown), such as but not limited to embodiments of the receiver/recorder device disclosed in U.S. Pat. No. 5,604,531 to Iddan et al. The telemetry unit 29 may operate via, for example, radio (RF) waves. The telemetry unit 29 may be constructed and operated similar to the transmitter 26 coupled to the antenna 27 of FIG. 1, but may also be differently constructed and operated as is known in the art for any suitable wireless or wired transmitter. For example, if the device 40 represents an imaging endoscope-like device or catheter-like device, the telemetry unit 29 may be replaced by a wired transmitter (not shown) as is known in the art. In other embodiments, a wired transmitter may be used with devices other than a catheter-like device. In such a case, the wired transmitter may transmit the imaged data to an external workstation (not shown) or processing station (not shown) or display station (not shown), for storage and/or processing and/or display of the image data.

The device 40 may also include a controller unit 45 which may be suitably connected to the imaging sensor 24A for, inter alia, controlling the operation of the imaging sensor 24A. The controller unit 45 may be any suitable type of controller, such as but not limited to, an analog controller, a digital controller such as, for example, a data processor, a microprocessor, a micro-controller, an ASIC, or a digital signal processor (DSP). The controller unit 45 may also comprise hybrid analog/digital circuits as is known in the art. The controller unit 45 may be suitably connected to the telemetry unit 29 and/or other units, for example, for controlling the transmission of image frames by the telemetry unit 29. In alternate embodiments, control may be achieved in other manners. For example, telemetry unit 29 may provide control or act as a controller.

The imaging device 40 typically includes one or more illumination units 23A which may be suitably connected to the controller unit 45. In accordance with one embodiment of the present invention, the illumination units 23A may include one or more red light source(s) 30A, one or more green light source(s) 30B, and one or more blue light source(s) 30C. The red light source(s) 30A, the green light source(s) 30B, and the blue light source(s) 30C may be controlled by the controller unit 45. The red light source(s) 30A as a whole may be considered an illumination unit, and similarly the green light source(s) 30B and blue light source(s) 30C may each be considered illumination units. The red light source(s) 30A, the green light source(s) 30B, and the blue light source(s) 30C may be controlled by the controller unit 45. For example, the controller unit 45 may send to the illumination unit 23A suitable control signals for switching on or off any of the red light source(s) 30A, the green light source(s) 30B, and the blue light source(s) 30C, or subgroups thereof as is disclosed in detail hereinafter.

Other colors and combinations of colors may be used. Typically, the illumination provided is visible light and, more specifically, different spectra of visible light, each of which forms a component of a color image. For example, one standard method of providing a color image provides to a viewer red, green and blue pixels, either in spatial proximity or temporal proximity, so that the three color pixels are combined by the viewer to form color pixels. Other sets of visible light forming color images may be used, or visible light not forming color images, and non-visible light may be used. If more than one light source is included within an illumination unit, the light sources may be spread from one another.

The red light source(s) 30A may have spectral characteristics suitable for providing red light which may be used for determining the reflection of light having a wavelength bandwidth within the red region of the spectrum. The spectrum of this red light source may be similar to the spectrum of white light after it was filtered by a typical red filter which may be used in the red pixels of an imager having a typical RGB type pixel triplet arrangement. Other types of red may be used.

Similarly, the green light source(s) 30B may have spectral characteristics suitable for providing green light which may be used for determining the reflection of light having a wavelength bandwidth within the green region of the spectrum. The spectrum of this green light source may be similar to the spectrum of white light after it was filtered by a typical green filter which may be used in the green pixels of an imager having a typical RGB type pixel triplet arrangement. Other types of green may be used.

Similarly, the blue light source(s) 30C may have spectral characteristics suitable for providing blue light which may be used for determining the reflection of light having a wavelength bandwidth within the blue region of the spectrum. The spectrum of this blue light source may be similar to the spectrum of white light after it was filtered by a typical blue filter which may be used in the blue pixels of an imager having a typical RGB type pixel triplet arrangement. Other types of blue may be used.

The exact spectral distribution of the red, green and blue light sources 30A, 30B, and 30C, respectively, may depend, inter alia, on the type and configuration of the light sources 30A, 30B, and 30C.

The light sources 30A, 30B, and 30C may be implemented differently in different embodiments of the present invention. Examples of usable light sources may include but are not limited to, light emitting diodes (LEDs) having suitable (e.g., red, green and blue) spectral characteristics, or other light sources capable of producing white light or approximately white spectral characteristics which may be optically coupled to suitable (e.g., red, green or blue) filters, to provide filtered light having the desired spectral output in the, e.g., red, green or blue parts of the spectrum, respectively. Thus, for example, a blue light source may comprise a white or approximately white light source (not shown) and a suitable blue filter. Green and red light sources may similarly include a white or approximately white light source, optically coupled to suitable green or red filter, respectively.

Such white or approximately white light sources may include LEDs, incandescent light sources, such as tungsten filament light sources, gas discharge lamps or flash lamps, such as for example small xenon flash lamps or arc lamps, or gas discharge lamps, or any other suitable white or approximately white light sources having a suitable spectral range which are known in the art.

The choice of the exact spectral characteristics of the light sources 30A, 30B and 30C, may depend, inter alia, on the sensitivity to different wavelengths of the imaging sensor 24A, on the application, or on other requirements.

The controller unit 45 may be (optionally) suitably connected to the imaging sensor 24A for sending control signals thereto. The controller unit 45 may thus (optionally) control the transmission of image data from the imaging sensor 24A to the telemetry unit 24 (or to a wired transmitter in the case of an endoscopic device, catheter-like device, or the like).

The device 40 may also include a memory unit 47. The memory unit 47 may include one or more memory devices, such as but not limited to random access memory (RAM) units, or other suitable types of memory units known in the art. The memory unit 47 may be used to store the image data read out from the imaging sensor 24A as disclosed in detail hereinafter.

The device 40 may also include one or more power sources 25A. The power source(s) 25A may be used for supplying electrical power to the various power requiring components or circuitry included in the device 40. It is noted that the electrical connections of the power source(s) 25A with the various components of the device 40 are not shown (for the sake of clarity of illustrations). For example, the power source(s) 25A may be suitably connected to the controller 45, the telemetry unit 29, the imaging sensor 24A, the memory unit 47, and the illumination units 23A.

Typically, for autonomous in vivo imaging devices, such as, but not limited to, the swallowable capsule-like device 10A of FIG. 1, the power sources may be batteries or electrochemical cells, as described for the power sources 25 of FIG. 1 The power source(s) 25A may also be any other type of suitable power source known in the art that may be suitably included within the device 40.

Figure 2B:
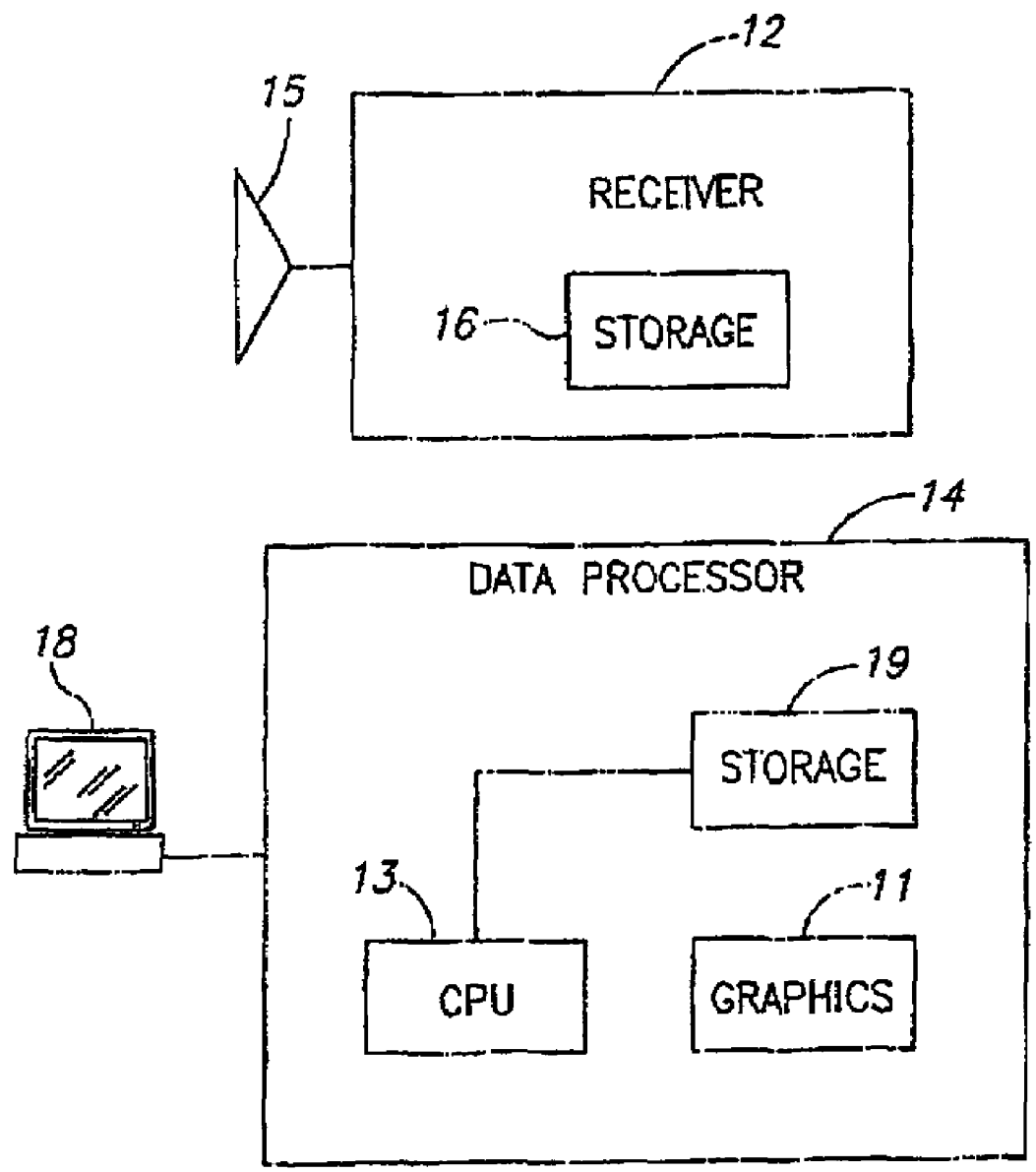
FIG. 2B depicts a receiving and a display system according to an embodiment of the present invention.

The power source(s) 25A may be any other suitable power source such as, for example, a mains operated direct current (DC) power supply or a mains operated alternating current (AC) power supply, or any other suitable source of electrical power For example, a mains operated DC power supply or a mains operated AC power supply may be used in a device 40 that may be implemented in an endoscope or catheter like device Typically, the device 40 is swallowed by a patient and traverses a patient's GI tract, however, other body lumens or cavities may be imaged or examined. The device 40 transmits image and possibly other data to components located outside the patient's body which receive and process the data. FIG. 2B depicts a receiving and a display system according to an embodiment of the present invention. Typically, located outside the patient's body in one or more locations, are a receiver 12, typically including an antenna 15 or antenna array, for receiving image and possibly other data from device 40, a receiver storage unit 16, for storing image and other data, a data processor 14, a data processor storage unit 19, a graphics unit 11, and an image monitor 18, for displaying, inter alia, the images transmitted by the device 40 and recorded by the receiver 12. Typically, the receiver 12 and receiver storage unit 16 are small and portable, and are worn on the patient's body during recording of the images.

Transmitter 26 may include control capability for, for example controlling the various operations of device 40, although control capability or one or more aspects of control may be included in a separate component. Transmitter 26 is typically an ASIC (application specific integrated circuit), but may be of other constructions; for example, transmitter 26 may be a processor executing instructions. Device 40 may include a processing unit separate from transmitter 26 that may, for example, contain or process instructions."

In an embodiment, all of the components may be sealed within the device body (the body or shell may include more than one piece); for example, an imager, illumination units, power units, and transmitting and control units, may all be sealed within the device body.

Device 40 typically may be or may include an autonomous swallowable capsule, but device 40 may have other shapes and need not be swallowable or autonomous.

Embodiments of device 40 are typically autonomous, and are typically self-contained. For example, device 40 may be a capsule or other unit where all the components are substantially contained within a container or shell, and where device 40 does not require any wires or cables to, for example, receive power or transmit information. Device 40 may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Typically, data processor 14, data processor storage unit 19 and monitor 18 are part of a personal computer or workstation which includes standard components such as a processor 13, a memory (e.g., storage 19, or other memory), a disk drive, and input-output devices, although alternate configurations are possible. Typically, in operation, image data is transferred to the data processor 14, which, in conjunction with processor 13 and software, stores, possibly processes, and displays the image data on monitor 18. Graphics unit 11 may, inter alia, form color images from discrete frames of monochrome data, and may perform other functions. Graphics unit 11 may be implemented in hardware or, for example, in software, using processor 13 and software. Graphics unit 11 need not be included, and may be implemented in other manners.

In alternate embodiments, the data reception and storage components may be of another configuration, and other systems and methods of storing and/or displaying collected image data may be used. Further, image and other data may be received in other manners, by other sets of components.

Typically, the device 40 transmits image information in discrete portions. Each portion typically corresponds to a precursor image or frame which is typically imaged using one colored light source spectrum, rather than a broad white spectrum For example, the device 40 may capture a precursor image once every half second, and, after capturing such an image, transmit the image to the receiving antenna Other capture rates are possible. Other transmission methods are possible. For example, a series of frames of data recorded with different colors (e.g., R, G, B) may be recorded by the capsule and sent in sequence or as one data unit. In a further embodiment, different frames recorded with different colors may be combined by the capsule and transmitted as one image. Typically, the image data recorded and transmitted is digital image data, although in alternate embodiments other image formats may be used. In one embodiment, each precursor frame of image data includes 256 rows of 256 pixels each, each pixel including data for brightness, according to known methods. The brightness of the overall pixel may be recorded by, for example, a one byte (i e., 0-255) brightness value. Other data formats may be used.

Reference is now made to FIG. 3 which is a schematic timing diagram illustrating an exemplary timing schedule which may be usable for performing color imaging in the imaging device illustrated in FIG. 2A.

The horizontal axis of the graph of FIG. 3 represents time (in arbitrary units). An exemplary imaging cycle 41 (schematically represented by the double headed arrow labeled 41) begins at time TB and ends at time TE. Each imaging cycle may include three different imaging periods 42, 43 and 44. In one embodiment, the imaging cycles are of fixed duration, such as one half second (for two images per second). Other imaging rates may be used, and the imaging cycles need not be of fixed duration. Furthermore, if different numbers of illumination spectra are used, different numbers of imaging periods may be used. For example, an RGBY illumination sequence may require four imaging periods. In alternate embodiment, lights or illumination spectra other than RGB may be used; for example, CMY or other spectra may be used.

Typically, within each period within an imaging cycle, illumination of a certain spectrum or color is provided, and a precursor image is captured using this illumination. Typically, each precursor image captured within an imaging cycle represents substantially the same view of the area to be imaged, as the images are captured within an image capture cycle lasting a relatively short amount of time For example, given a certain rate of movement, capturing a set of images one half second apart within an image cycle generally results in substantially the same view being imaged in each of the periods. Other rates of imaging may be used, depending on the expected rate of movement. The illumination is provided by a plurality of illumination units, each unit including one or more lights which, as a whole, produce illumination of a certain color. The one or more lights of an illumination unit may be spatially separate The illumination differs among the periods, to produce images created using different colors reflected to the imager, although, within a cycle, certain colors or spectra may repeat. The order of the colors is typically unimportant, although in some embodiments, the order may be significant.

For example, within the duration of the first imaging period 42 (schematically represented by the double headed arrow labeled 42), imaging is performed using red illumination. For example, the controller unit 45 of the device 40 (FIG. 2A) may switch on or energize the red light source(s) 30A for the duration of the red illumination period 42A (schematically represented by the double headed arrow labeled 42A) The duration of the period in which the red light source(s) 30A provides red light is schematically represented by the hatched bar 47. During the red illumination period 42A, the red light is reflected from (and/or diffused by) the intestinal wall or any other object which is imaged, and part of the reflected and diffused red light may be collected by the optical system 22A (FIG. 2A) and projected on the light sensitive pixels of the imaging sensors 24A. The pixels of the imaging sensor 24A are exposed to the projected red light to produce a precursor image.

After the red illumination period 42A is terminated (by switching off of the red light source(s) 30A by the controller unit 45), the pixels of the imaging sensor 24A may be read out or scanned and transmitted by the telemetry unit 29 to an external receiver/recorder (not shown), or may be stored in the memory unit 47. Thus, a first image is acquired (and may be stored) which was obtained under red illumination. The pixel scanning may be performed within the duration of a first readout period 42B (schematically represented by the double headed arrow labeled 42B).

After the first readout period 42B ends, a second imaging period 43 may begin Within the duration of the second imaging period 43 (schematically represented by the double headed arrow labeled 43), imaging is performed using green illumination. For example, the controller unit 45 of the device 40 (FIG. 2A) may switch on or energize the green light source(s) 30B for the duration of the green illumination period 43A (schematically represented by the double headed arrow labeled 43A). The duration of the period in which the green light source(s) 30B provide green light is schematically represented by the hatched bar 48. During the green illumination period 43A, the green light is reflected from (and/or diffused by) the intestinal wall or any other object which is imaged and part of the reflected and diffused green light may be collected by the optical system 22A (FIG. 2A) and projected on the light sensitive pixels of the imaging sensors 24A. The pixels of the imaging sensor 24A are exposed to the projected green light.

After the green illumination period 43A is terminated (by switching off of the green light source(s) 30B by the controller unit 45), the pixels of the imaging sensor 24A may be read out or scanned and transmitted by the telemetry unit 29 to an external receiver/recorder (not shown), or may be stored in the memory unit 47. Thus, a second image is acquired (and may be stored) which was obtained under green illumination. The pixel scanning may be performed within the duration of a second readout period 43B (schematically represented by the double headed arrow labeled 43B).

After the second readout period 43B ends, a third imaging period 44 may begin. Within the duration of the third imaging period 44 (schematically represented by the double headed arrow labeled 44), imaging is performed using blue illumination. For example, the controller unit 45 of the device 40 (FIG. 2A) may switch on or energize the blue light source(s) 30C for the duration of a blue illumination period 44A (schematically represented by the double headed arrow labeled 44A). The duration of the period in which the blue light source(s) 30C provide blue light is schematically represented by the hatched bar 49. During the blue illumination period 44A, the blue light is reflected from (and/or diffused by) the intestinal wall or any other object which is imaged and part of the reflected and diffused blue light may be collected by the optical system 22A (FIG. 2A) and projected on the light sensitive pixels of the imaging sensors 24A The pixels of the imaging sensor 24A are exposed to the projected blue light.

After the blue illumination period 44A is terminated (by switching off of the blue light source(s) 30B by the controller unit 45), the pixels of the imaging sensor 24A may be read out or scanned and transmitted by the telemetry unit 29 to an external receiver/recorder (not shown), or may be stored in the memory unit 47. Thus, a third image is acquired (and may be stored) which was obtained under blue illumination. The pixel scanning may be performed within the duration of a third readout period 44B (schematically represented by the double headed arrow labeled 44B).

After the ending time TB of the first imaging cycle 41, a new imaging cycle (not shown) may begin as is disclosed for the imaging cycle 41 (by repeating the same imaging sequence used for the imaging cycle 41). In alternate embodiments illumination from more than one illumination unit may be used per image. For example, while capturing an image, both a set of blue lights (wherein set may include one light) and a set of yellow lights may be used. Within an imaging cycle, certain illumination periods may use the same or substantially the same spectrum of light. For example, there may be two "blue" illumination periods.

It is noted that if the device 40 does not include a memory unit 47, the time periods 42B, 43B, and 44B may be used for transmitting the acquired "red" "green" and "blue" images to the external receiver/recorder or to the processing workstation.

Alternatively, if the image data of the "red" "green" and "blue" images acquired within the duration of an imaging cycle (such as the imaging cycle 41, or the like) are stored within the memory unit 47, the stored "red" "green" and "blue" images of the imaging cycle may be telemetrically transmitted to a receiver/recorder or processing workstation after the imaging cycle 41 is ended.

After the (e.g., red, green and blue) acquired images have been transferred from the receiver/recorder to a processing and display workstation (or after the three images have been transmitted by wire to such a processing and display workstation, for example, in the case of endoscope-like or catheter-like device, or the like), the images data may be processed to produce the final color image for display. Since, typically, each of the different precursor images captured within an imaging cycle represents substantially the same view, combining these images produces that view, but with different color characteristics (e g., a color image as opposed to monochrome) This may be performed by suitably processing the values of the (gray scale) light intensity data of the same pixel in the, e.g., three ("red", "green", and "blue") imaged data sets. Typically, each monochrome precursor image includes grayscale levels which correspond to one color or spectrum (e.g., levels of red).

For example, each corresponding pixel (typically a monochrome pixel) in a set of images collected using various colors may be combined to produce color pixels, where each resulting color pixel is represented or formed by a set of color levels (e.g., RGB levels) and may include sub-pixels (e.g., one color pixel including RGB sub-pixels). Pixels may be repeatedly combined the within the set of precursor images to produce a final image. In one type of typical monitor, each color pixel is represented by a set of monochrome (e.g, RGB) pixels, and/or by a set of color levels (e.g. RGB color levels).

Other methods may be used. This computation may be corrected (e.g., brightness levels) to account for different sensitivity of the imaging sensor 24A to different wavelengths of light as is known in the art, and other processing, correction or filtering may be performed.

In one embodiment, data processor 14 (FIG. 2B) combines each frame of the series of sets of image frames to produce a series of color images for display monitor 18 or for storage or transmission. The image data is read out from data processor storage unit 19 and processed by, for example, graphics unit 11. Various methods may be used to combine the color image data, and a separate graphics unit need not be used. Other systems and methods of storing and for displaying collected image data may be used.

Figure 4:
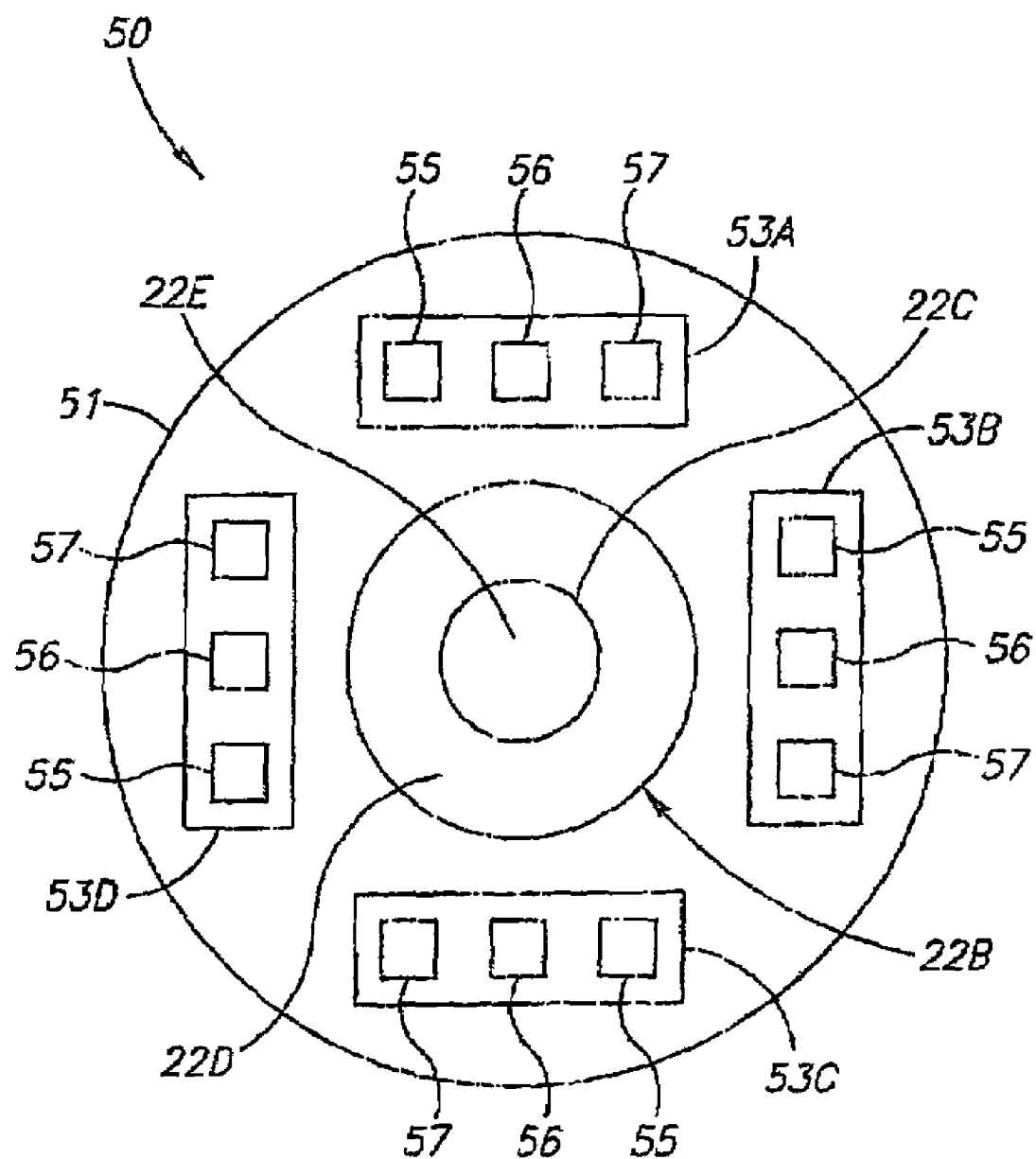
FIG. 4 is a schematic front view diagram illustrating an exemplary configuration of light sources having different spectral characteristics relative to the optical system of an in vivo imaging device, in accordance with an embodiment of the present invention.

Reference is now made to FIG. 4 which is a schematic front view diagram illustrating an exemplary configuration of light sources having different spectral characteristics relative to the optical system of an in vivo imaging device, in accordance with an embodiment of the present invention.

The device 50 of FIG. 4 is illustrated in front view and may be similar in shape to, for example, the device 10A of FIG. 1. The optical window 51 of the device 50 may be similar to the dome shaped optical window 21 of the device 10A of FIG. 1; other configurations may be used. The front part of the optical system 22B may include an optical baffle 22D having an opening 22C therethrough. A lens 22E (seen in a frontal view) may be attached within the baffle 22D. Four illumination elements 53A, 53B, 53C, and 53D are arranged attached within the device 50 as illustrated. Typically, the four illumination elements 53A, 53B, 53C and 53D are configured symmetrically with respect to the optical system 22B. In alternate embodiments, other components or arrangements of components may be used. For example, other numbers of illumination elements may be used, and a baffle or other elements may be omitted.

Each of the four illumination elements 53A, 53B, 53C, and 53D includes, for example, a red light source 55, a green light source 56 and a blue light source 57. The light sources 55, 56 and 57 may be LEDs having suitable red, green and blue emission spectra as disclosed hereinabove. Alternatively, the light sources 55, 56 and 57 may be any other suitable compact or small light sources comprising a combination of a white or approximately white light source and a filter having a suitable red, green and blue bandpass characteristics as disclosed hereinabove. Other colors ay be used, and light sources other than LEDs may be used.

The light sources 55, 56 and 57 each may be considered a set of different light units (wherein set may include one), each light unit outputting a different spectrum or color. The spectra used may overlap in whole or in part—i.e., in some embodiments, two blue units outputting similar or same blue light may be used, or in some embodiments, two light units outputting different colors may have spectra that overlap to an extent. Each light unit may include one or more lamps. While in the embodiment shown, each light unit includes four spatially separated lamps, other numbers of lamps and patterns may be used.

In operation the device 50 may use a similar illumination schedule as disclosed for the device 40 (an example of one schedule is illustrated in detail in FIG. 3). All the red light sources 55 may be switched on within the duration of the time period 42A (FIG. 3) and terminated at the end of the time period 42A. All the green light sources 56 may be switched on within the duration of the time period 43A (FIG. 3) and terminated at the end of the time period 43A. All the blue light sources 57 may be switched on within the duration of the time period 44A (FIG. 3) and terminated at the end of the time period 44A. The advantage of the light source configuration of the device 50 is that the red, green and blue light sources may distribute the light relatively evenly to achieve relatively uniform light distribution in the field of view of the optical imaging system 22B (FIG. 4). Other configurations may be used, such as configurations not using different banks of colored lights.

It is noted that while the specific light source configuration illustrated in FIG. 4 is suitable for performing an embodiment of the color imaging method of the present invention, many other different light source configurations including different numbers of light sources, different spectra and colors, and different types of light sources may be used. Moreover, the number and the geometrical arrangement of the red, green and blue light sources 55, 56, and 57, respectively, within the four illumination elements 53A, 53B, 53C, and 53D may be different. Furthermore, the number of the illumination elements and their arrangement with respect to the optical system 22B may also be varied.

It is noted that the color imaging method and device disclosed hereinabove need not be limited to methods and devices using RGB illumination sources or the RGB method for color imaging. Other types of color imaging methods may also be used. For example, in accordance with another embodiment of the present invention the light source(s) 30A, 30B, and 30C may be adapted for used with the CYMK method which is well known in the art, by using light sources producing light having cyan, yellow and magenta spectral characteristics as is known in the art. This adaptation may be performed, for example, by using white or approximately white or broadband light sources in combination with suitable cyan, yellow and magenta filters Other, different spectral color combinations known in the art may also be used The use of the CYMK color method may also require proper adaptation of the data processing for color processing and color balancing.

It is noted that the RGB or CYMK illuminating method disclosed hereinabove may have the advantage that they may allow the use of an imaging sensor having a third of the number of color pixels used in a conventional color imager having pixel triplets (such as, but not limited to red, green, and blue pixel triplets or cyan, yellow, and magenta pixel triplets, or the like). In this way, one may reduce the size and the light sensitive area of the imaging sensor without reducing the nominal image resolution.

The use of, for example, the three color illumination periods disclosed hereinabove for an embodiment of the present invention, may provide three temporally separate exposures of the imaging sensor to three different types of colored light, may have other advantages. For example, in the RGB example disclosed hereinabove, the three consecutive exposures of the same pixels to red, green and blue light, the data available after the completion of an imaging cycle includes the intensity of red, green and blue light values which were measured for each pixel of the imaging sensor. It is therefore possible to directly use the measured values for displaying a color image which may simplify the data processing and may improve the resolution and the color quality or fidelity (such as, for example, by reducing color aliasing effects). This is in contrast with other color imaging methods, used in imaging sensors having color pixels arranged in triplets or other arrangement types on the imaging sensor, in which it is necessary to perform the post-processing computations for interpolating or approximating the approximate color intensity at each pixel by using the data of the surrounding pixels having different (or complementary) colors.

It is noted that for autonomous in vivo imaging devices which may be moved through, for example, the GI tract or through other body cavities, caution must be exercised in choosing the duration of the imaging cycle and of the duration of the illumination time periods 42A, 43A and 44A, and the duration of the readout time periods 42B, 43B, and 44B In some embodiments, the duration of these time periods should be as short as possible to reduce the probability that the device 40 may be moved a substantial distance in the GI tract (or other body cavity or lumen) within the duration of any single imaging cycle. If such a substantial movement of the device 40 occurs within the duration of a single imaging cycle, the "red", "green" and "blue" acquired images may not be identical (or in other words may not properly register), which may introduce errors in the processing of the final color image which may in turn cause the color image to be blurred or smeared or distorted or not representative of the shape or the true color of the imaged object. Thus, typically, each of the different precursor images captured within an imaging cycle captures substantially the same image or view (e.g., the same view of a portion of an in-vivo area), using a different color or spectrum. Significant movement in between images may result in a different view being imaged. Of course, where movement is less of a problem, timing may be less of an issue In insertable devices such as endoscopes or catheter-like devices, the device may be held relatively static with respect to the imaged object, which may allow the use longer duration of the illumination time periods 42A, 43A and 44A, and the duration of the readout time periods 42B, 43B, and 44B.

Figure 5A:
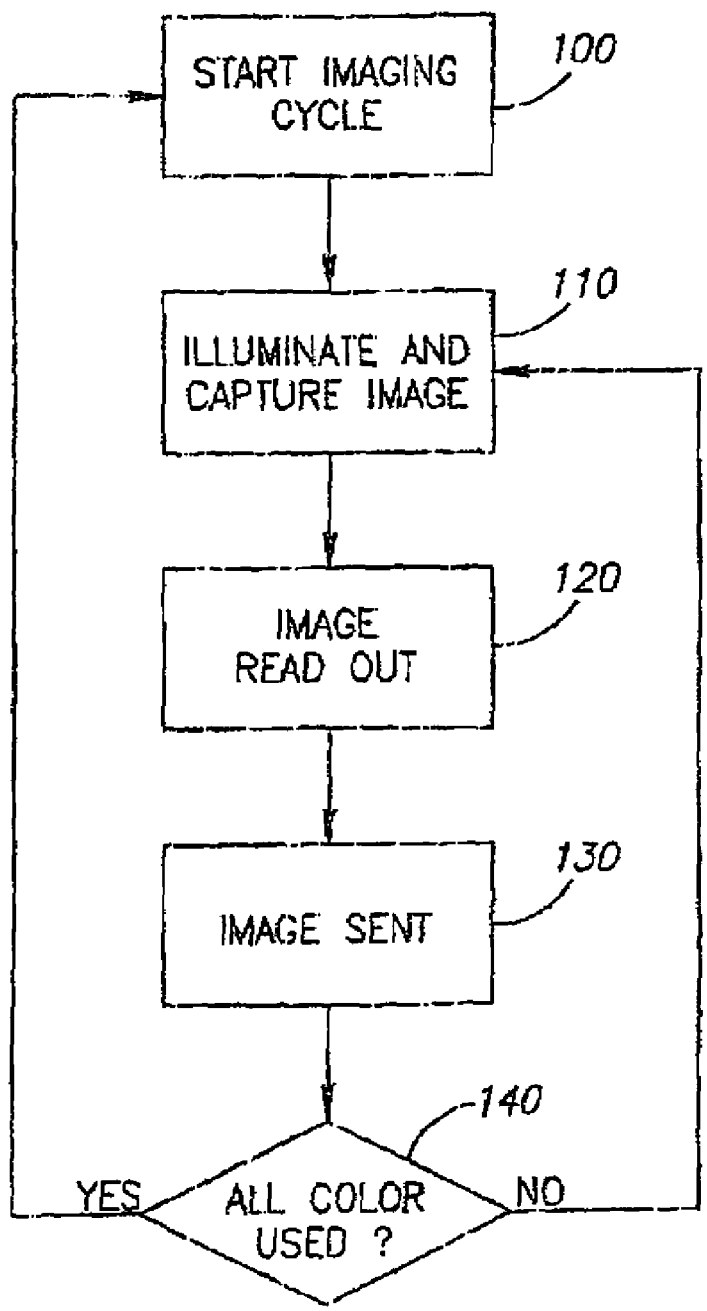
FIG. 5A illustrates a series of steps of a method according to an embodiment of the present invention.

FIG. 5A illustrates a series of steps of a method according to an embodiment of the present invention. Referring to FIG. 5A, in step 100, an imaging cycle starts.

In step 110, a single color or spectrum of light illuminates an area to be imaged, and an image is captured. Typically, step 110 is repeated at least once more with another color or spectrum of light.

In step 120, the image is read out to, for example, a memory device or transmitter. In alternate embodiments, no image readout separate from transmission, processing, or storage need be used.

In step 130, the image is transmitted or otherwise sent to a receiving unit In an alternate embodiment, the image data may simply be recorded or stored, or the set of images comprising a color image may be sent at the end of an image cycle.

In step 140, if all of the set of colors or spectra have been used to capture an image, the image cycle process starts again at step 100 If further colors or spectra are to be used, the method proceeds to step 110 to image using that color or spectrum.

In alternate embodiments, other steps or series of steps may be used.

Figure 5B:
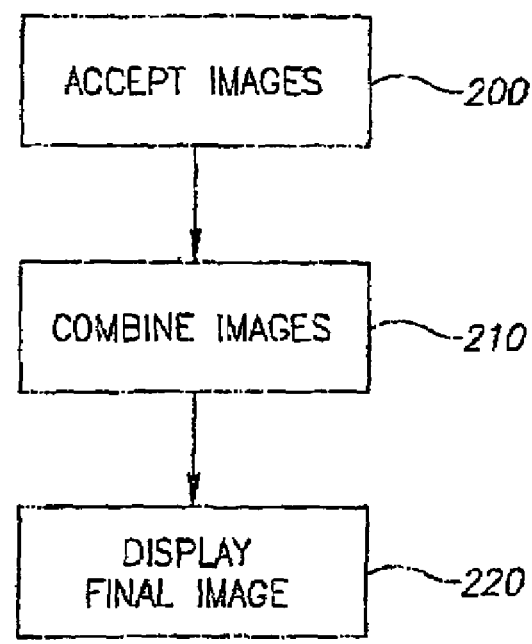
FIG. 5B illustrates a series of steps of a method according to an embodiment of the present invention.

FIG. 5B illustrates a series of steps of a method according to an embodiment of the present invention. Referring to FIG. 5B, in step 200, a processor accepts a set of precursor images from, for example, an in vivo imaging device. Typically, each precursor image is a monochrome image created using a non-white light or spectrum, and represents the same view.

Figure 6:
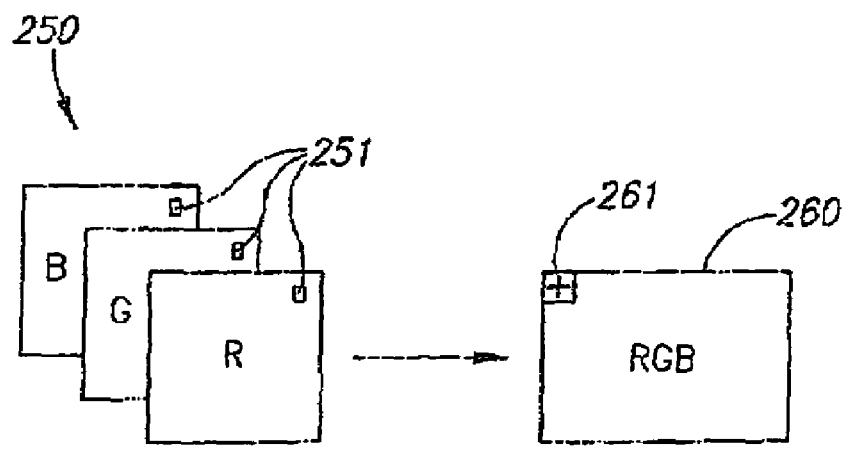
FIG. 6 illustrates a set of precursor images and a final image according to an embodiment of the present invention.

In step 210, the set of precursor images is combined to form one final image. For example, referring to FIG. 6, a set of images 250, containing pixels such as pixels 251, may be combined to produce a final image 260, containing composite pixels such as pixel 261. In the example shown in FIG. 6, a set of R, G and B pixels 251, each typically representing substantially the same area of an image, are combined to form one pixel 261, which may include, for example, RGB sub-pixels. Other image formats and other methods of combining images may be used; for example, the final image may include temporal combination of colors.

In step 220, the final image may be displayed to a user. Alternately, the image may be stored or transmitted In alternate embodiments, other steps or series of steps may be used.

Figure 7:
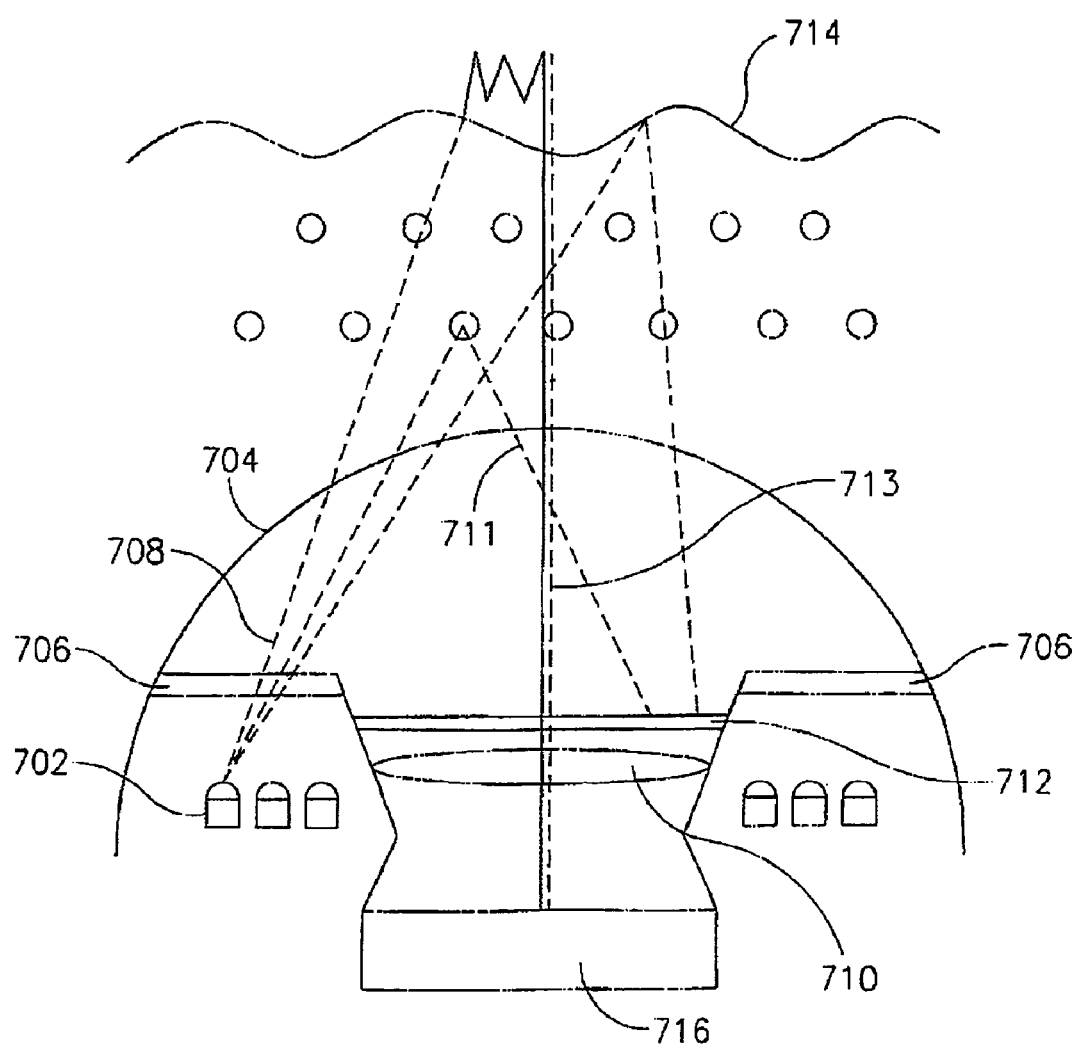
FIG. 7 illustrates a schematic functional block diagram of an in vivo imaging device with a polarized filter, in accordance with an embodiment of the present invention.

FIG. 7 illustrates a schematic functional block diagram of an in vivo imaging device with a polarized filter, in accordance with an embodiment of the present invention. In some embodiments, one or more illumination units 702 may be situated or configured under dome 704. Dome 704 may in some embodiments have optical properties. Under, attached to, or included in dome 704 may be a polarizer or polarizing filter 706 that may polarize light or light beams 708 emitted by for example illumination unit 702. In some embodiments, filter 706 may block, prevent or impede for example horizontally polarized light beams 708 (or other orientations or types of beams) emitted by illumination unit 702 from passing filter 706, such that vertically polarized beams 708 or rays may pass through filter 706. In some embodiments, one or more illumination units 702 may be housed under a filter that is separate from dome 704.

Optical system 710, which may be or include for example one or more lenses, may be partially or completely under or covered by a filter 712 such as for example a filter that permits light of only a particular polarization to pass through. In some embodiments, filter 712 may block, prevent or impede from reaching optical system 710 those light beams 708 that are polarized in the same polarization state (such as for example right polarized, left polarized, horizontally polarized, vertically polarized, or polarized at other angles) as the light beams 708 that passed through polarizer or polarized filter 706. Note that when used herein right, left, horizontal and vertical are relative terms, and other terms may be used depending on the perspective of the viewer.

In some embodiments, polarizer or polarizing filter 706 may be or include a linear polarizer that may permit horizontally polarized light beams to pass through. In some embodiments, light beams passing through polarizing filter 706 may be vertically polarized light beams. In some embodiments, polarizing filter 706 may be or include a circular polarizer. In some embodiments, polarizer or polarizing filter 706 may cover one of several illumination units 702.

In operation, polarized light passing through filter 706 may be directed towards for example a wall of a body lumen such as for example a gastrointestinal wall, which may be or include for example a target area 714 to be imaged. A turbid media such as for example chyme or other substances or particles in an area of a body lumen between an imager and a target area 714, may reflect light beam 708 specularly. Such specularly reflected light beam 711 may be reflected back to optical system 710 in the same polarized state as light beam 708 assumed when it passed through polarizer or polarized filter 706. For example, if polarizer or polarized filter 706 permits passage of horizontally polarized light beams 708, filter 712 may prevent horizontally polarized light beams from reaching optical system 710. In some embodiments, some or all of specularly reflected light beams 711 may be blocked by filter 712 from reaching optical system 710 and imager 716

In some embodiments light beams 708 that may reach a target area 714, such as for example a wall of a body lumen such as for example a gastrointestinal tract, may be diffused in such target area 714. Such diffusion may cause some of the light beams 713 that are reflected back to optical system 710 to assume a polarization state that is opposite to the polarization state of the light beams 708 that passed through filter 706. In some embodiments, such opposite polarized light beam 713 may pass through filter 712 and be for example captured in an image by imager 716.

In some embodiments, the blocking of a light beam 711 that may have been reflected from a turbid media, from particles suspended in a turbid media, from an outer surface of an endo-luminal wall or from other objects in between an in-vivo device and a target area 714 may alleviate some or all of the disruptive light or backscatter that may be associated with imaging objects through a turbid media.

In some embodiments, polarizer or polarizing filter 706 may be or include a fixed position filter that may polarize all or most light beams 708 passing through it that are emitted by illumination unit 702. In some embodiments, polarizing filter 708 may be activated or deactivated over selected parts of for example dome 704.

Figure 8:
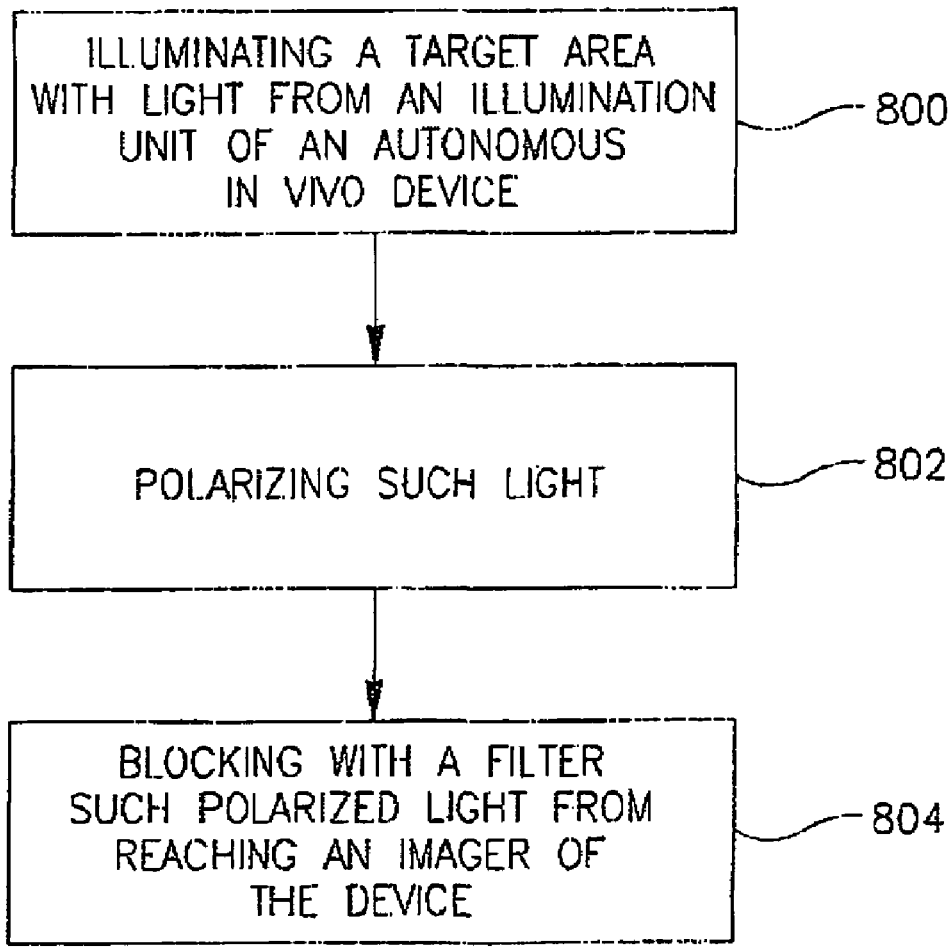
FIG. 8 is a block diagram of a method of blocking light reflected from a turbid media from reaching an imager, in accordance with an embodiment of the invention.

Reference is made to FIG. 8, a block diagram of a method of blocking light reflected from a turbid media from reaching an imager, in accordance with an embodiment of the invention. In block 800, a target area of for example an endoluminal wall may be illuminated with light from an illumination unit of an autonomous in vivo device.

In block 802, light from an illumination unit may be polarized, to assume for example a first polarized state by for example a polarizer or polarization filter.

In block 804, a filter may block light in such first polarized state from reaching an imager of an autonomous device.

In some embodiments, blocking the light polarized in a first polarized state may include blocking specularly reflected light that was reflected back from a turbid media such as for example chyme or other liquids or particles in for example an endoluminal cavity.

In some embodiments, a target area may be illuminated with more than one monochromatic illumination unit at a time, and one or more of such units may be activated separately and at different periods from other such units. In some embodiments, light beams from an illumination unit may be polarized to a first polarization state in a first period, and to a second polarization state in a second period. In some embodiments, an alteration in the polarization of light beams may be accomplished by an alteration of for example a configuration or orientation of a polarizing filter covering an illumination unit.

In some embodiments, a switch or other control unit (e g, a control unit part of the transmitter or a controller within the in-vivo device) may activate a monochromatic illumination unit that emits light beams in a particular wavelength, or in a particular band of wavelengths, and may coordinate the activation of such illumination unit with the activation of an imager that may capture image data of the target area as the target area is illuminated with such light beams. A switch may activate another illumination unit emitting light beams at another wavelength, or may activate an imager that may capture image data of the target area as the target area is illuminated with light of such other wavelength. Image data from a first image illuminated at a first wavelength may be subtracted from image data from a second image that is illuminated at a second wavelength. In some embodiments, calculations and processing such as subtracting image data may be performed in a unit external to a patient's body.

The illumination units may be, for example, LEDs or other suitable units emitting certain wavelengths of light, or may include filters to produce certain wavelengths of light.

Figure 9:
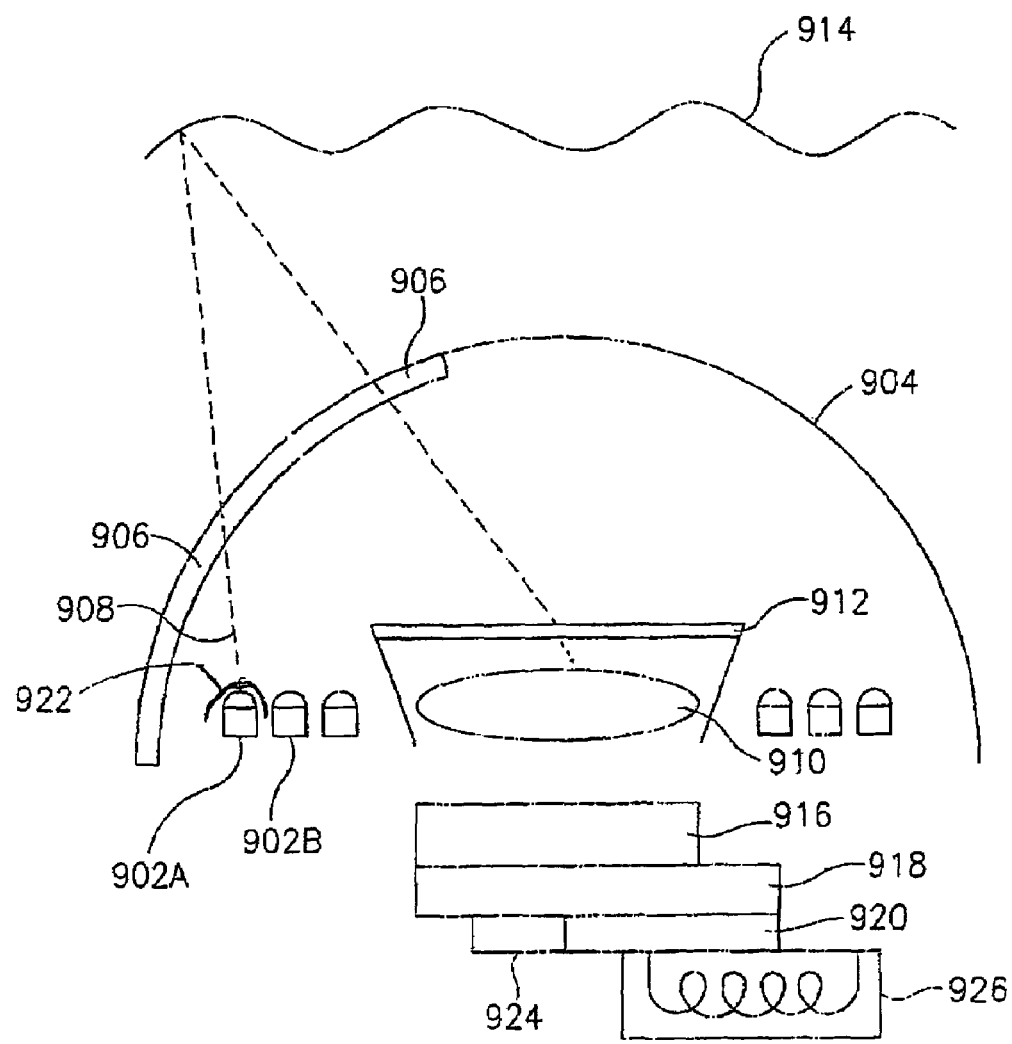
FIG. 9 illustrates a illustrates a schematic functional block diagram of an in vivo imaging device with a monochromatic illuminator and a polarizing filter in accordance with an embodiment of the invention.

Reference is made to FIG. 9, a schematic diagram of an autonomous in vivo imaging device with a monochromatic illuminator and polarizing filter in accordance with an embodiment of the invention. In some embodiments, a liquid crystal filter 906 may for example be included or built into for example a section, arc or area of for example dome 904. In some embodiments, a filter or polarizer such as for example a liquid crystal filter 906 may cover or filter only one or some of illumination units 902 and may be separate from dome 904. Such separate cover may be in the form of for example a curved dome 922 that may cover one, two or more illumination units 902. In some embodiments, a curved dome may be configured in a shape approximating a half or hemisphere with illumination unit 902 situated in the center of a base of the hemisphere. In some embodiments light beams emitted from such illumination unit 902 may strike dome 922 orthogonally. Other configurations of dome 922 are possible, and other positioning of illumination unit 902 are possible. In some embodiments, a plurality of light beams emitted by an illumination unit 902 at a plurality of angles may orthogonally strike filter 906 and such filter may be configured on dome 904, on small dome 922 or elsewhere. In some embodiments, filter 906 may polarize light beams at angles of up to +/−60 degrees In some embodiments, filter 906 may be activated over some or less than all of the areas of dome 904 that cover illumination units 902. In some embodiments, activating filter 906 may include activating a liquid crystal on or over one or more designated parts of for example dome 904. In some embodiments polarizing filter 906 may be activated or deactivated by for example the application of for example an electric current or other signal to liquid crystal filter 906 or to one or more areas of dome 904. In some embodiments a polarization effect produced by filter 906 may be altered from for example a horizontal polarization to a vertical polarization by for example the application of a current or signal that may alter the configuration or orientation of filter 906. For example, upon the application of a designated signal or current to a particular portion or area of dome 904, filter 906 may be activated to permit for example horizontally polarized light to pass through it. Upon the application of another designated signal or current to a same or different portion or area of dome 904, filter 906 may be activated for example to let vertical light pass through it.

In some embodiments, illumination unit 902 may be or include for example a light emitting diode or other light source that may emit for example white light. In some embodiments illumination unit 902 may be or include a light emitting diode or other light source that emits monochromatic light. In some embodiments, one or more monochromatic illumination unit 902 may be included in an autonomous in vivo device. In some embodiments, simultaneous activation of some or all of such illumination units 902 may generate a white light. In some embodiments one or more of illumination units 902 may emit light or light beams with a wavelength of between for example 300 nm to for example 450 nm. Image data captured during such illumination may be useful in for example observing a surface of an endoluminal wall. In some embodiments one or more of illumination units 902 may emit light or light beams with a wavelength of between for example 450 nm to for example 700 nm. Image data captured during such illumination may be useful in for example detecting colors of an endoluminal wall. In some embodiments one or more of illumination units 902 may emit light or light beams with a wavelength of between for example 700 nm to for example 1100 nm. Image data captured during such illumination may be useful in for example observing a sub-surface layer of an endoluminal wall. Other wavelengths, other ranges of wavelengths, and other number of illumination units 902 may be used.

In some embodiments a filter 912 may be situated over or covering optical system 910 and imager 916. In some embodiments, all or some of the light reaching imager 916 may be filtered by filter 912 In some embodiments, filter 912 may block or prevent light from reaching optical system 910 and imager 916, if such light is polarized in the same polarization state as the light that passed through filter 906 For example, in some embodiments, if polarizer 906 polarizes light so that only left polarized light passes through filter 906, then filter 912 may be configured to prevent left polarized light from passing through to optical system 910 and imager 916. Other configurations of filter 906 and filter 912 may be used to prevent or stop other light in other polarization states from reaching optical system 910 and imager 916.

In operation, an illumination unit 902A may be activated to emit for example a monochromatic light or monochromatic light beams 908 at a wavelength of for example 900 nm. During all or a portion of the period during which illumination unit 902A is activated, polarizing filter 906 may be activated to polarize the monochromatic light emitted by illumination unit 902A so that the light beams permitted to pass through filter 906 towards a target area 914 are for example right polarized. Some or all of the light beams 908 that may be reflected back to filter 912 may be specularly reflected from for example a body tissue such that they are reflected back while still in a right polarization state. Filter 912 may permit right polarized light but not other light to pass through to optical system 910 and to imager 916

In some embodiments, illumination unit 902A may be activated or remain activated, and a change may be triggered in the polarization function of for example filter 906. In some embodiments, such change may be or include an alteration in the polarization state of the light that is permitted to pass through filter 906. For example after such alteration, filter 906 may permit a left polarized light beam 908 to pass through filter 906. In some embodiments, the polarization state of light permitted to pass through filter 906 may be the opposite of the polarization state of the light that had been permitted to pass through such filter 906 before such alteration was made. In some embodiments, the polarization function of filter 912 may remain unchanged regardless of the alteration of a polarization function of filter 906.

In some embodiments, the process described above of altering a polarization function of filter 906 may facilitate a calculation of the amount of specularly reflected light reflected back to imager 918 through filter 912 from a target area 914, relative to the amount of diffused light reflected back to imager 918 through filter 912 from target area 914. In some embodiments, a particular proportion of specularly reflected light that is reflected back from a target area 914 relative to diffused light reflected back from such same area, may be for example an indicator of a pathological condition in such target area 914.

In some embodiments, another illumination unit 902B may be activated in a period when illumination unit 902A is for example deactivated. In some embodiments, illumination unit 902B may emit light in for example a shorter wavelength, such as for example 650 nm, than the light emitted by for example illumination unit 902A. In some embodiments, illumination unit 902B may emit a longer wavelength light beam than illumination unit 902A Other configurations are possible. In some embodiments, filter 906 may be configured to permit light to pass through it when such light is polarized in a state opposite to the light permitted to pass through filter 912 When so configured, light reaching imager 916 may include light that was diffused in a target area 914, but may not include light that was specularly reflected back to imager 918 without being diffused in a body tissue.

In some embodiments, a processor such as for example processor 918 that may be attached to imager 916 or that may be included in an autonomous in vivo sensing device, may subtract image data produced by a light with a short wavelength that was diffused in target area 914 from image data produced for example by light with a long wavelength that was diffused in target area 914. In some embodiments, the image data resulting from such subtraction may provide an image of an inner or subsurface layer of target area 914.

In some embodiments, processor 918 may be located outside of an autonomous device such as for example, in an external receiver of image data that may be located for example outside of a patient's body.

In some embodiments, image data may be collected during for example one or more illumination periods of illumination unit 902A and 902B, and such image data may be stored in a data storage unit or memory 920 of an autonomous in vivo device. For example, an image may be collected during one or more illumination periods of for example illuminator 902 when filter 906 was set to polarize light in a first polarization state, and another image may be collected when filter 906 was set to polarize light in a second polarization state. The image data collected in memory 920 may include more than one image, and may be transmitted to an external receiver in for example batches.

In some embodiments a switch 924 may coordinate the activation and deactivation of one or more illumination units 902 and of the polarization function of for example filter 906. For example, switch 924 may time the activation of illumination unit 902A and filter 906 so that during a particular period when illumination unit 902 is activated, filter 906 first polarizes light passing through it into a horizontal state of polarization, and then polarizes light passing through it into a vertical state of polarization Switch 924 may also direct imager 916 to capture an image of a target area 904 when such area is illuminated with light beams horizontally polarized, and another image when the target area is illuminated with light beams vertically polarized. Similarly, switch 924 may activate illumination unit 902B and filter 906 to polarize light emitted by illumination unit 902B in a first polarized state and then in a second polarized state. Switch 924 may time imager 916 to capture an image of target area 914 as it is illuminated by light in such first polarized state, and to capture an image of a target area 914 as it is illuminated by light in such second polarized state.

In some embodiments, a memory 920 may store images or image data of target area 914 as it is illuminated by illumination unit 902 with light polarized in a first polarization state and in a second polarization state In some embodiments one illumination unit 902 may emit light in a first wavelength, such as 770 nm, and another of illumination units 902 may emit light in a second wavelength, such as for example 690 nm. Image date from the image illuminated at 690 nm may be subtracted from image data from the image illuminated at 770 nm, to produce an image of a subsurface layer of endoluminal tissue.

In some embodiments, a transmitter 926 may, on a periodic basis, transmit image data stored in memory 920. In some embodiments, a transmission of image data may be made upon the completion for example of a cycle of images that may include for example an image of a target area 914 illuminated with light of a first wavelength in a first polarized state and/or in a second polarized state, and an image of such target area 914 illuminated with light of a second wavelength in a first polarized state and/or in a second polarized state.

In some embodiments a cycle of illumination from two or more illumination units 902 with light in a first and a second polarization state may include for example three, four or more images. Various suitable periods or lengths of a cycle are possible, and other number of illuminations and image captures are possible.

In some embodiments an autonomous in vivo device may be immobilized in a body lumen, and the images in one or more cycles of illuminations may be captured when the device is held in a single position adjacent to a target area 904

While the invention has been described with respect to a limited number of embodiments, it will be appreciated that many variations, modifications and other applications of the invention may be made which are within the scope and spirit of the invention.

Embodiments of the present invention may include apparatuses for performing the operations herein. Such apparatuses may be specially constructed for the desired purposes (e.g., a "computer on a chip" or an ASIC), or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein Unless specifically stated otherwise, as apparent from the discussions herein, it is appreciated that throughout the specification discussions utilizing terms such as "processing", "computing", "calculating", "determining", or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

We claim:

1. An autonomous in vivo device comprising:
    an illumination unit;
    a polarizer to polarize light from said illumination unit;
    an imager;
    a filter to block said polarized light from reaching said imager of said autonomous in vivo device; and
    a controller to coordinate an illumination by said illumination unit with an activation of said polarizer.

2. The device as in claim 1, comprising an optical dome over said illumination unit, said optical dome comprising said polarizer.

3. The device as in claim 2, wherein said polarizer comprised in said optical dome is configured orthogonally to a plurality of light beams emitted by said illumination unit.

4. The device as in claim 2, wherein said polarizer is a curved polarizer.

5. The device as in claim 1, wherein said filter is to block said polarized light that is specularly reflected from a turbid media.

6. The device as in claim 1, wherein said filter is to allow light in a polarization opposite to said polarized light to reach said imager.

7. The device as in claim 6, wherein said light in a polarization opposite to said polarized light comprises light that was diffused in an endo-luminal tissue.

8. The device as in claim 1, comprising a plurality of illumination units surrounding said imager.

9. The device as in claim 1, wherein said polarizer includes a liquid crystal.

10. The device as in claim 1, wherein said controller is to coordinate an illumination by said illumination unit with an activation of said imager.

11. The device as in claim 1, comprising a plurality of monochromatic illumination units, a first of said plurality of monochromatic illumination units to emit light having a wavelength of between 300 nm and 450 nm, a second of said monochromatic illumination units to emit light having a wavelength of between 450 nm and 700 nm, and a third of said plurality of monochromatic light units to emit light having a wavelength of between 700 nm and 1100 nm.

12. The device as in claim 1, comprising a plurality of monochromatic illumination units.

13. The device as in claim 12, wherein said controller is configured to activate a first monochromatic illumination unit independently of a second monochromatic illumination unit.

14. The device as in claim 12, wherein said controller is to coordinate:
    an activation of a monochromatic illumination unit of said plurality of monochromatic illumination units to emit a monochromatic light beam; and
    an activation of said polarizer, said activation of said polarizer to:
        polarize, in a first polarization state, a light beam emitted from said monochromatic illumination unit; and
        polarize, in a second polarization state, a light beam emitted from said monochromatic illumination unit.

15. The device as in claim 14, comprising a memory to store image data collected by said imager, said image data comprising:
    image data of a target area illuminated by a light beam polarized in a first polarization state; and
    image data of said target area illuminated by a light beam polarized in said second polarization state.

16. The device as in claim 1, comprising a transmitter to transmit image data to an external data receiver.

17. The device as in claim 1, wherein said polarizer is to polarize said light in a first polarization state, and to polarize said light in a second polarization state.

18. The device as in claim 1, comprising an immobilizer to immobilize said device adjacent to an endoluminal target area.

19. A system comprising:
    an autonomous in vivo sensing device comprising:
        a plurality of monochromatic illumination units;
        a polarizer to polarize light from said illumination units;
        an imager; and
        a controller to coordinate an illumination by at least one of said plurality of monochromatic illumination units with an activation of said polarizer.

20. The system as in claim 19, comprising a processor, said processor to subtract:
    image data of a target area, said target area illuminated by a first monochromatic illumination unit, from
    image data of said target area, said target area illuminated by a second monochromatic illumination unit.

21. The system as in claim 19, wherein a first of said plurality of monochromatic illumination units is to emit a light beam having a wavelength of between 300 nm and 450 nm, a second of said monochromatic illumination units is to emit a light beam having a wavelength of between 450 nm and 700 nm, and a third of said monochromatic illumination units is to emit a light beam having a wavelength of between 700 nm and 1100.

22. The system as in claim 19, comprising a filter to block polarized light from reaching said imager.

23. A method comprising:
    illuminating a target area with light from an illumination unit of an autonomous in vivo sensing device;
    obtaining an image of said illuminated target;
    polarizing said light;
    blocking with a filter said polarized light from reaching an imager; and
    obtaining a polarized image of said illuminated target.

24. The method as in claim 23, wherein blocking said polarized light from reaching said imager, comprises blocking said polarized light that was specularly reflected from a turbid media.

25. The method as in claim 23, wherein said illuminating a target area comprises illuminating said target area with light from a plurality of monochromatic illumination units.

26. The method as in claim 25, comprising:
   illuminating said target area with said plurality of monochromatic light beams;
   activating one of said monochromatic illumination units;
   activating another of said monochromatic illumination units and subtracting:
      image data of said target area illuminated by said one of said monochromatic illumination units, from
      image data of said target area illuminated by said another of said monochromatic illumination units.

27. The method as in claim 23, wherein said illuminating said target area comprises illuminating said target area with a plurality of monochromatic light beams wherein:
   a first light beam is at a wavelength of between 300 nm and 450 nm;
   a second light beam is at a wavelength of between 450 nm and 700 nm; and
   a third light beam is at a wavelength of between 700 nm and 1100 nm.

28. The method as in claim 23, wherein said polarizing said light comprises:
   polarizing to a first polarization state a first of a plurality of light beams; and
   polarizing to a second polarization state a second of said plurality of light beams.

* * * * *